United States Patent

Satake

[11] Patent Number: 4,574,636
[45] Date of Patent: Mar. 11, 1986

[54] APPARATUS FOR EXAMINING AN OBJECT BY USING ULTRASONIC BEAMS

[75] Inventor: Nozomi Satake, Ootawara, Japan

[73] Assignee: Kabushiki Kaisha Toshiba, Japan

[21] Appl. No.: 613,828

[22] Filed: May 24, 1984

[30] Foreign Application Priority Data

May 26, 1983 [JP] Japan .................................. 58-92676

[51] Int. Cl.[4] ............................................ G01N 29/00
[52] U.S. Cl. .......................................... 73/607; 73/620
[58] Field of Search ................. 73/606, 607, 620, 625, 73/626; 367/7, 11; 358/112; 128/660

[56] References Cited

U.S. PATENT DOCUMENTS

| 4,212,072 | 7/1980 | Hualsman et al. | 358/112 |
| 4,310,907 | 1/1982 | Tachita et al. | 73/626 |
| 4,368,643 | 1/1983 | Tachita et al | 73/626 |
| 4,375,671 | 3/1983 | Engle | 358/112 |
| 4,381,675 | 5/1983 | Roberts et al. | 73/606 |
| 4,417,475 | 11/1983 | Okazaki | 73/606 |

FOREIGN PATENT DOCUMENTS 2912957 10/1980 Fed. Rep. of Germany ........ 73/607

Primary Examiner—Stephen A. Kreitman
Attorney, Agent, or Firm—Finnegan, Henderson, Farabow, Garrett & Dunner

[57] ABSTRACT

In an ultrasonic examination apparatus of the sector scanning type, a false contour appears in a tomographic image of an object due to a variation of the pixelizing, or digitizing precision over the entire scanning region, especially near the central ultrasonic scanning lines. A wobbling processor is provided in an address generator for write operation. When the echo signals, or the image signals obtained by the scanning of the central untrasonic scanning lines are written into pixels of a frame memory, the write-in addresses are processed by the wobbling processor so that the pixelizing precision can be made relatively uniform over the entire scanning region.

5 Claims, 7 Drawing Figures

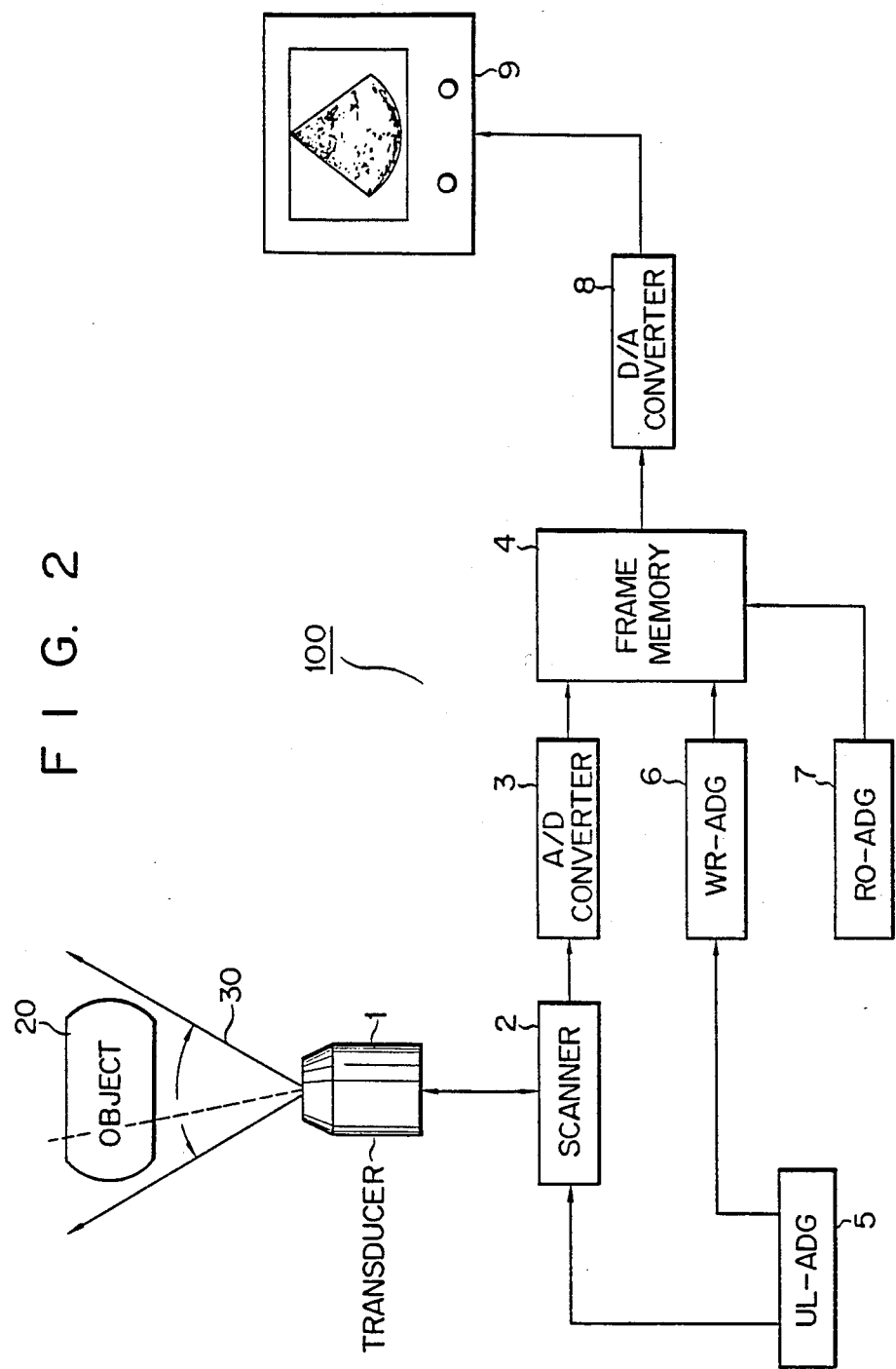

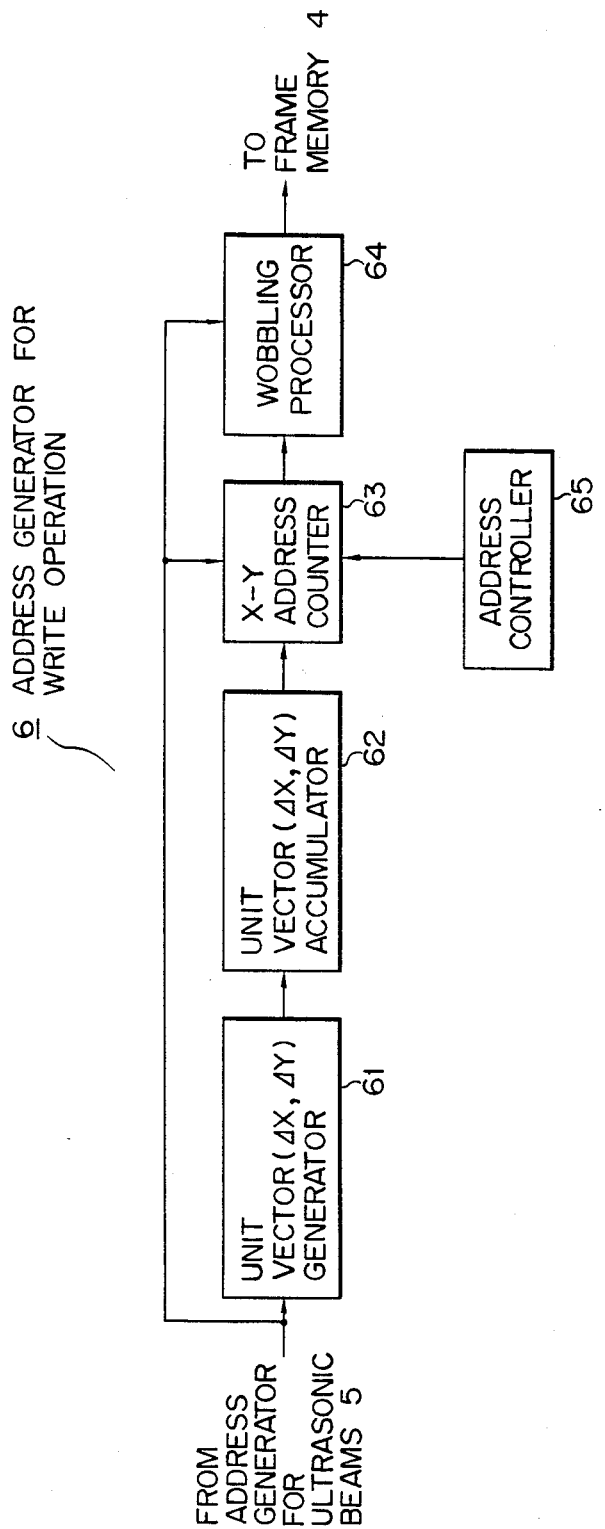

APPARATUS FOR EXAMINING AN OBJECT BY USING ULTRASONIC BEAMS

BACKGROUND OF THE INVENTION

1. Field of the Invention

The present invention generally relates to an apparatus for examining an object by using ultrasonic beams, and particularly to an apparatus in which a sectional area in the object is scanned by the ultrasonic beams and ultrasonic echo signals derived from reflections by boundaries and discontinuities therein are processed in an image processing method.

2. Description of the Prior Art

In general, such an apparatus is essentially comprised of an ultrasonic transducer having a plurality of ultrasonic transducer elements in an array alignment, a scanning unit which excites those ultrasonic transducer elements to generate a plurality of ultrasonic beams and which then scans a plurality of those ultrasonic beams in a sector form so as to obtain echo signal data of the object, a frame memory unit in which the echo signal data is temporarily stored in relation to the ultrasonic beams, and a TV monitor on which a sector-scanned tomographic image of the object is displayed in a real time.

The above-identified sector-scanning type ultrasonic imaging apparatus is known from, e.g., U.S. Pat. No. 4,368,643 issued on Jan. 18, 1983 to Tachita, and U.S. Pat. No. 4,310,907 issued on Jan. 12, 1982 to Tachita.

In such a sector scanning type ultrasonic imaging apparatus, there are the following problems. Since the echo signal data is stored in the given memory position (i.e., pixel) of the frame memory corresponding to the ultrasonic scanning line, the pixelizing, or digitizing precision on the ultrasonic scanning lines in a direction perpendicular to the television scanning direction, i.e., the horizontal scanning direction becomes vry high. On the other hand, the quantizing precision is kept constant, so that a false contour appears in the displayed image.

In other words, in the frame memory, a screen of TV monitor is divided in a matrix form to allocate the memory address to its corresponding pixel, and the column direction of the matrix is coincident with the television scanning direction, i.e., the horizontal scanning direction and also the row direction of the matrix is coincident with the vertical scanning direction, or a direction perpendicular to the longitudinal axis of the array of the ultrasonic transducer elements. The ultrasonic scanning lines are directed from the upper side toward the lower side of a TV screen at angles corresponding to the travelling directions thereof. Namely the echo signal data is stored in the pixels of the frame memory along the imaginarily-drawn lines in such a manner that the signal data on a depth of the object is stored. Accordingly, as the directions of the ultrasonic scanning lines, i.e., those of the imaginarily-drawn lines, are coincident with the orientation of the pixels, the pixelizing precision becomes high with respect to the direction perpendicular to the television scanning direction. However, the directions of the ultrasonic scanning lines are not sufficiently coincident with the orientation of the pixels, so that a substitution pixel is selected to store the echo signal data. This pixel is located adjacent to the pixel which the ultrasonic scanning line originally intersects (i.e., the simple pixelizing operation, or simple digitizing operation).

As a result, when such a frame memory is read out in synchronism with the television horizontal scanning, the readout signal is superimposed with the sync pulses (i.e., the composite video signal), and the resultant video signal is displayed on the TV monitor, the ultrasonic scanning lines are not displayed as straight lines in the any directions except the television vertical scanning direction and the diagonal of the pixels.

In general, the brightness information data of the ultrasonic diagnostic apparatus is processed by a bit length of approximately 6 bits in view of the grey scale of the TV monitor and also the processing speed of the image data. Accordingly the same sampling precision is realized in any position of the ultrasonic scanning line. That is, available gradation is kept constant. On the other hand, since it is known that a smoothing image can be recognized if a balance is maintained between the pixelizing precision and quantizing precision, the following drawback will occur. In such a digitized image the quantizing precision of which is kept constant, but only the pixelizing precision of which becomes high in the certain position of the scanning line, a false contour such as a contour line may occur therein.

As previously described, in the sector scanning type ultrasonic examination apparatus, the image data is temporarily stored in the frame memory and then is read out in conformity with the television scanning system so as to display it on the TV monitor. Consequently, as the directions of the ultrasonic scanning lines change in a shape of a sector, the pixelizing precision varies in accordance with the scanning line positions, especially the pixelizing precision for the lines near a center of the sector scanning region which becomes too high in comparison with that for other scanning line positions. As a result, the above-described false contour occurs.

Moreover, this false contour may cause not only vague images, but also errors in diagnosis. Accordingly, an improvement is strongly required in this field.

It is therefore an object of the present invention to mitigate such drawbacks and to provide an apparatus for examining an object by using ultrasonic beams, in which a false contour can be prevented without degrading the image quality, the false contour being caused when the quantizing precision is kept constant and only the pixelizing, or digitizing precision changes in accordance with the positions of the ultrasonic scanning lines.

SUMMARY OF THE INVENTION

The above object and other objects and features of the present invention may be achieved by providing an apparatus for examining an object ultrasonically comprising:

ultrasonic transducer means facing the object and having a plurality of ultrasonic transducer elements aligned in an array;

means for exciting the ultrasonic transducer elements to generate a plurality of ultrasonic beams, for scanning toward the object the ultrasonic beams in a sector form, and for receiving through the ultrasonic transducer means a plurality of ultrasonic echo signals derived from reflections by boundaries and discontinuities in the object;

A/D converting means for converting the ultrasonic echo signals produced from the scanning means into corresponding digital echo signals;

means for temporarily storing the digital echo signals in a plurality of pixels arranged in a matrix pattern;

first means for generating a first address signal supplied at least to the scanning means so as to control travelling directions of the ultrasonic beams;

second means for generating a second address signal in response to the first address signal as a write-in address signal being supplied to the memory means so that the digital echo signals from the A/D converting means are written in the pixels of the matrix pattern in relation to the travelling directions of the ultrasonic beams;

third means for generating third address signal as a readout address signal, the readout address signal being supplied to the memory means so that the stored digital echo signals are read out therefrom in readout directions adapted to television scanning directions;

D/A converting means for converting the read digital echo signals into corresponding analogue echo signals; and a television monitor means for processing the analogue echo signals so as to display on its screen a tomographic image of the object in a sector shape.

BRIEF DESCRIPTION OF THE DRAWINGS

The invention is best understood by reference to the accompanying drawings, of which:

FIG. 2 is a schematic block diagram of the ultrasonic examining apparatus according to one preferred embodiment;

FIG. 3 is a schematic block diagram of the interval circuit of the address generator for write operation shown in FIG. 2;

DETAILED DESCRIPTION OF THE PREFERRED EMBODIMENTS

Before describing the preferred embodiments it is believed that, the following definitions of terms will be greatly helpful to understand the technical scope and spirit of the present invention.

Figure 1:
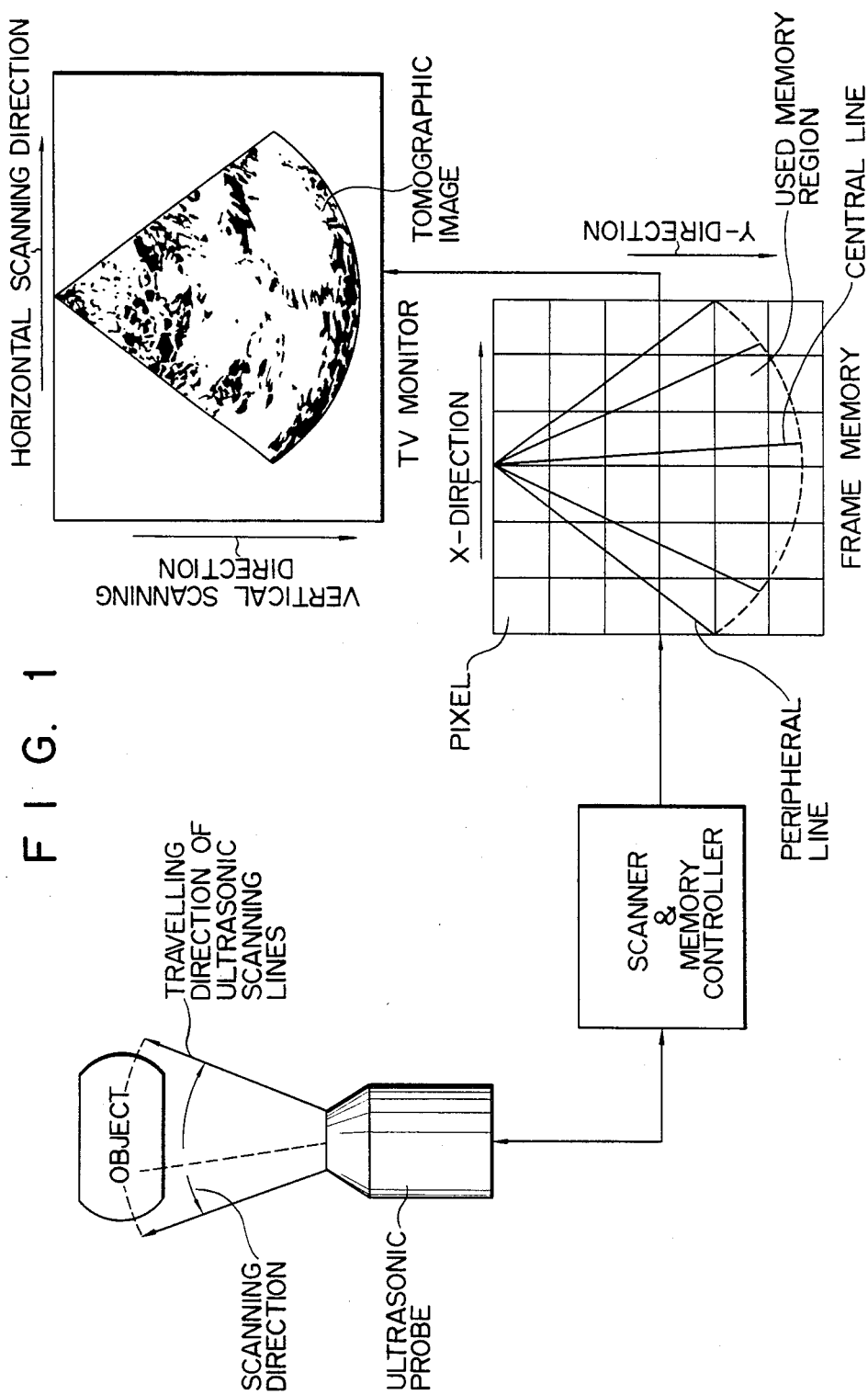
FIG. 1 is an illustration for explaining various definitions that are employed in the present specification.

The illustration in FIG. 1 does not serve to define the technical scope and spirit of the invention, but merely illustrates the various definitions and the basic idea according to the invention. Referring to FIG. 1, the travelling direction of the ultrasonic scanning lines and their scanning direction are shown. Further, since a plurality of the ultrasonic scanning lines, i.e., the ultrasonic beams, are sequentially scanned as shown in FIG. 1, the outline of the scanned ultrasonic beams indicates a sector. The beams are therefore called sector scanning type ultrasonic beams.

In the frame memory, a plurality of pixels are arranged in a matrix. A column of the matrix is defined as the "X direction" and a line is defined as the "Y direction". For the sake of understanding, the memory region of the frame memory used to store the sector and the ultrasonic scanning lines are imaginarily drawn. The ultrasonic scanning lines that are illustratively located around the peripheral region in the frame memory region are defined as "peripheral lines", and those located near the central region thereof are defined as "central lines".

In the television monitor, the tomographic image of the object is displayed in the sector shape. The horizontal scanning direction is "the television (TV) scanning direction" in the present specification. This TV scanning direction is coincident with the X-direction of the frame memory. The central line of the ultrasonic scanning lines is substantially parallel to the vertical scanning direction of the TV monitor.

FIG. 2 shows a block diagram of an ultrasonic examination apparatus 100 according to the invention.

A sector scanning type ultrasonic transducer 1 is provided, in which a plurality of ultrasonic transducer elements are aligned in an array and from which a plurality of ultrasonic beams, or scanning lines 30 are sequentially generated toward an object, e.g., a patient 20 in a sector form as shown in FIG. 2. For example, 48 ultrasonic transducer elements (not shown in detail) are employed and excited at approximately 4 MHZ. Then, 128 ultrasonic scanning lines (beams) are generated. The beam is scanned for an interval of 1/30 sec. Accordingly, since this scanning of the ultrasonic beams is in synchronism with the field scanning of a TV monitor, a scanned image of the object 20 can be displayed on the TV monitor without the specific processing.

Transducer 1 also receives the ultrasonic beams 30 which have reflected from boundaries and discontinuities in the object 20, and transforms them into electrical signals known as echo signals.

Those operations of the ultrasonic beams, e.g. the scanning of generated beams and the transforming of received beams, are controlled by a scanner 2.

The echo signals leave scanner 2 and are converted by an A/D converter 3 into corresponding digital echo signals. The digital echo signals are then temporarily stored in a frame memory 4 having a plurality of pixels in a matrix form. An address 5 generator for ultrasonic beams (scanning lines) is connected, on one hand, to the scanner 2 and, on the other hand, to the frame memory 4 via an address generator 6 for write operation.

The address generator 5 for ultrasonic beams produces an address information signal which corresponds to the scanning positions of the ultrasonic beams 30. Upon receipt of this address information signal, the scanner 2 controls the travelling angles for the ultrasonic beams 30 accordingly became the address information corresponds to the travelling directions.

The function of the address generator 6 for write operation is "dither" or "wobbling" processing as one of the image processings. The dither or wobbling processing is carried out in such a manner that when the address information signal is supplied to the address generator 6, the digital echo signal derived from the A/D converter 3 is written in the given pixels of the frame memory 4 after the dither or wobbling address is added thereto. That is, the digital echo signals which are obtained during the scanning of the ultrasonic scanning lines 30 in a direction perpendicular to the television horizontal scanning direction are stored along a zigzag line (an imaginarily-drawn dot line on the pixels of the frame memory 4), and the digital echo signals which are obtained during the same scanning in other direction are stored along the normal line (i.e., the simple pixelizing, or simple digitizing).

An address generator 7 for readout operation is connected to the frame memory 4. The readout addresses are supplied from the address generator 7 to the frame memory 4, so that the digital image data signals (in other words, the digital echo signals) are sequentially read out therefrom in synchronism with the television scanning. That is, the readout speeds in both X and Y directions for the frame memory 4 are synchronized with the horizontal and vertical TV scanning times (in other words, the line and field scanning times) (see FIG. 1). A D/A converter 8 is connected to the frame memory 4 to convert the digital image signals readout into analogue image signals. A TV monitor of the standard television system 9 is connected to the D/A converter 8. The tomographic image of the scanned object 20 can be displayed on the TV monitor 9 in a sector form as shown in FIGS. 1 and 2.

FIG. 3 shows a block diagram of an internal circuit of the address generator for write operation 6. This address generator 6 is constructed by a unit vector generator 61, a unit vector accumulator 62, an X-Y address counter 63, an address controller 65 and a wobbling processor 64. The unit vector generator 61 is connected to receive the address information signals from the address generator 5 for ultrasonic beams, the signals denoting the scanning position Nos. 1 to 128 of the ultrasonic scanning lines 30. The address information signals are also supplied to the X-Y address counter 63 and the wobbling processor 64. Upon receipt of the address information signals, the generator 61 produces unit vectors (ΔX, ΔY) that represent the deflection directions, or the travelling angles of the ultrasonic beams 30, those directions, or angles being determined by the address information signals.

The unit vector accumulator 62 is connected to the unit vector generator 61, whereby the output unit vectors (ΔX, ΔY) are accumulated every sampling intervals for the detection of the ultrasonic echo signals. The X-Y address counter 63 is connected to the unit vector accumulator 62. When the accumulated results are supplied to the address counter 63, the addresses required for storing the digital image data signals in the frame memory 4 are derived from the counter 63.

The wobbling processor 64 is connected to receive those addresses from the address counter 63. This wobbling processor 64 functions as follows.

The dither values, or wobbling values are preset in the wobbling processor 64. If the address information signals produced from the address generator 5 are coincident with addresses for designating the scanning positions of the central and adjoining lines 30 with respect to the sector scanning, those dither values or wobbling values are added to the addresses for the frame memory 4 which are output from the X-Y address counter 63. In other words, when the address information signals correspond to the addresses (write-in addresses) for designating the scanning positions of the central and its adjacent scanning lines 30, i.e., the travelling directions substantially perpendicular to the television scanning direction or the horizontal scanning direction, the wobbling process is carried out in the wobbling processor 64. Consequently, the digital echo signals which have been derived from the scanning positions of the central and its neighboring scanning lines 30, are written in the given pixels of the frame memory 4 by the wobbling-processed write-in addresses produced from the wobbling processor 64. As a result, a trail for connecting the stored pixels represents a zigzag line (see the dot line of FIG. 4B). This operation is defined as "the dithering or wobbling pixelizing".

If the address information signals are coincident with the addresses of the scanning lines 30 other than the above-described central and its adjacent lines, the addresses derived from the X-Y address counter 63 are directly applied to the frame memory as the write-in addresses. This operation is defined as "the simple pixelizing, or simple digitizing".

Then, the unit vector accumulator 62 and the address counter 63 have a self reset function respectively, whereby those circuit elements are cleared whenever the addresses for the ultrasonic scanning lines change. The address controller 65 is connected to the X-Y address counter 63 so that after the counter 63 is cleared, the write-in addresses in the address counter 63 are initilized to the starting position for the scanning operation. This position is designated by such addresses for representing pixel positions of the start point of the lines 30.

A description will now be made of an operation of the ultrasonic examination apparatus 100.

As previously explained, the number of the ultrasonic scanning lines, or ultrasonic beams, 30 in the preferred embodiment; is selected to 128. The address information signals for indicating the 1st to the 128th lines are thus sequentially and repeatedly generated from the address generator for ultrasonic beams 5 at a given time interval. Since those address information signals are applied to the scanner 2 and the address generator for write operation 6, the transducer 1 is controlled by the scanner 2 in such a manner that the ultrasonic beams 30 are transmitted/received in the travelling directions which are predetermined by those address information signals. Then the echo signals are obtained by the transducer 1, and converted in the A/D converter 3 into the digital echo signal.

On the other hand, as the address information signal is also applied to the address generator 6 for write operation, address generator 6 updates the write-in address in such a manner that this address corresponds to a depth direction of the object 20 along the travelling direction of the ultrasonic beams 30, while the address in the scanning direction is changed with respect to the transmit time of the echo signal.

The digital echo signals are temporarily stored in the frame memory 4 based upon the write-in addresses from the address generator 6 for write operation. Accordingly, in the matrix of pixels of the frame memory 4 having one frame capacity, an image data is stored which includes the echo signal levels (i.e., brightness signal levels) for the ultrasonic beams in the travelling directions and at the scanning positions according to the depth direction.

While the address information signals are updated in turn in the address generator 5, the ultrasonic beams 30 are scanned in a sector form, so that a plurality of image data is subsequently stored in the frame memory 4, which has been obtained in accordance with the scanning positions. Accordingly, the memory region of the frame memory 4, into which the image data is actually stored, has a sector shape as shown in FIG. 1. In other words, the image data is not stored in the entire memory region of the frame memory 4 except the above sector-shaped memory region.

In connection with the storage condition of the image data in the frame memory 4, the addreess generator 6 for write operation has the following features: the dither, or wobbling values are added to the write-in address when the scanning data is obtained by the central and its adjacent scanning lines 30, and, no wobbling value is added to the addresses of the remaining scanning lines 30 (i.e., the simple pixelizing or the simple digitizing).

Figure 4A:
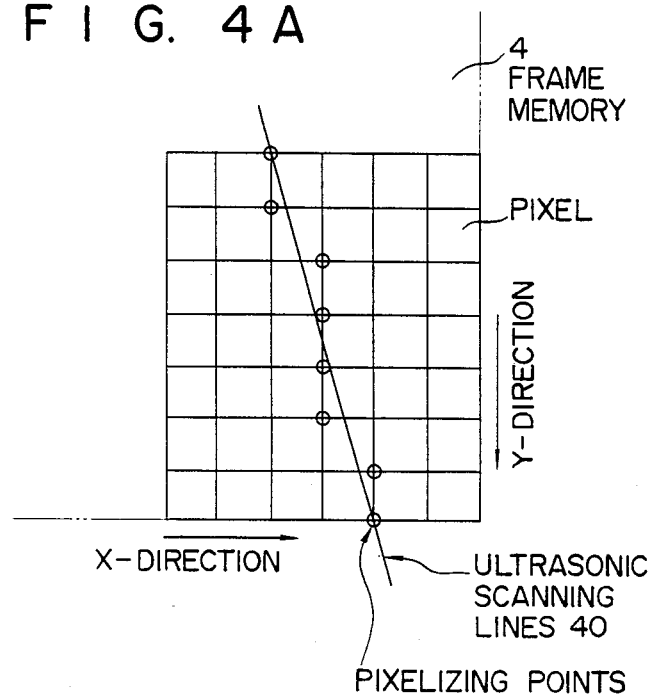
FIGS. 4A and 4B shows schematic illustrations for explaining the pixelizing or digitizing operations.
Figure 4B:
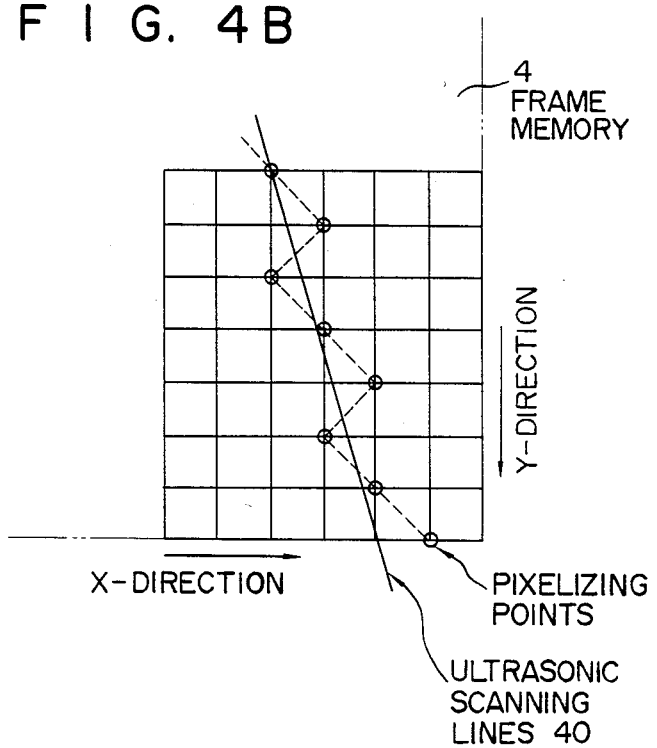

For a better understanding, a detailed description will now be given to the wobbling operation according to the invention, as compared with the simple pixelizing. FIG. 4A illustratively shows how to perform the simple pixelizing. That is to say, the matrix-shaped pixels of the frame memory 4 are particularly shown, on which an ultrasonic scanning line 40 is imaginarily drawn. As already described with reference to the FIG. 1, the echo signal data that is obtained by the scanning lines, except the central lines, e.g., the peripheral lines, as stored in the pixels closes to the scanning line 40 (see the pixelizing points of FIG. 4A). The above-described write-in operation is called "the simple pixelizing, or the simple digitalizing".

On the other hand, the echo signal data that is obtained by the central and its adjacent scanning lines are stored in the pixels along a zigzag line. That is, the echo signal data are stored in the pixels of the frame memory 4 in such a manner that a trail of the pixelizing points has a zig-zag line (see the dotted line of FIG. 4B). Such a write-in operation is so-termed as "the dithering", or "wobbling pixelizing" in the specification.

The wobbling pixelizing is understood as follows. In accordance with the scanning positions of the ultrasonic beams 30, the pixelizing precision is varied. For example, the pixelizing precision, or the resolution of the central lines, becomes higher than that of the peripheral lines.

It should be noted that, as previously described, the brightness component of the echo signal is quantized in 6 bits, i.e., a 64 step tone, and this quantizing precision is kept fixed over the entire scanning positions.

A description will then be made of the unit vector generator 61. This generator 61 generates the unit vectors ($\Delta X$, $\Delta Y$) in response to the address information signal derived from the address generator 5. Those unit vectors ($\Delta X$, $\Delta Y$) are real numbers by which adequate pixel positions (X and Y coordinate positions) are obtained. The positions are allocated by the simple pixelizing for the echo signal data in accordance with the matrix construction of the frame memory 4. For instance, if the unit vectors ($\Delta S$, $\Delta Y$) are given to 0.71 respectively with respect to a certain steering direction, or travelling direction of the ultrasonic beams 30, those values of 0.71 are accumulated in the unit vector accumulator 62 of every sampling interval of and at the sampling frequency of the A/D converter 3. Then when there is a carry, or a digit reduction between the decimal fraction part and the integer part of the accumulated values, count values of the X-Y address counter 63 which represent addresses of pixel positions in the X and Y direction, are incremented or decremented by one respectively.

The wobbling processor 64 operates as follows. To generate a display as if the ultrasonic scanning line 40 would be the zig-zag line (see FIG. 4B), the write-in address derived from the X-Y address counter 63 is summed by a certain value (the wobbling value) corresponding to approximately 1 pixel only in the X direction so as to be shifted from the original address. This is equal to such a case that if the pixel position in the television vertical scanning line or in the Y direction of the frame memory 4 is counted in the nth notation, e.g., the binary notation, the addition of the wobbling value is controlled whether the least significant digit is "1" or "0".

It should be understood that the count values of the X-Y address counter 63 designate the coordinate positions in the X and Y directions that are measured from the starting position of the ultrasonic beam, so that those are also available as the address data for the frame memory 4.

An operation of the address generator for write operation 6 will now be described in detail with reference to FIG. 3 and a flow chart in FIG. 5.

When the unit vector generator 61 receives the address information signals from the address generator for ultrasonic beams 5, the unit vectors ($\Delta X$, $\Delta Y$) are produced by which the proper pixel positions of the simple pixelizing can be obtained in connection with the pixel arrangement of the frame memory 4. Those unit vectors are accumulated by the unit vector accumulator 62 at the sampling interval (=data sampling interval corresponding to one pixel in the ultrasonic beam).

The unit vector accumulator 62 continues to produce the unit vectors ($\Delta X$, $\Delta Y$) whenever the accumulated values become the predetermined values, whereby the address counter 63 counts up and thus the count values are output as the write-in address for the frame memory 4.

The address information signal of the address generator 5 is also applied to the wobbling processor 64. If the wobbling processor 64 recognizes, for example, the generation of the 64th and 65th ultrasonic scanning lines, the dither or wobbling value is added to the output address of the X-Y address counter, so that the final write-in address is obtained for the frame memory. This is the dithering or wobbling processing operation. If it recognizes the generation of the remaining ultrasonic scanning lines, no wobbling value is added to the output address which is the simple pixelizing operation. As previously explained, the wobbling values are added to the output address of the address counter 63 in order that the imaginary ultrasonic scanning lines wobble in the frame memory 4. For example, the wobbling processor 4 can judge whether the pixel position in the Y direction of the frame memory 4 is an even number, or an odd number, whereby it may control to add the wobbling value to the output address of the counter 63 in the X direction of the frame memory 4.

As a result, if the wobbling processing operation is required, the wobbling value is added to the address data in the X direction of the output address in relation to the address position in the Y direction, so that the address data is shifted by the wobbling value in the X direction. Consequently, as those output addresses of the address counter 63 for the 64th and 65th ultrasonic scanning lines are processed in the wobbling processor 64, the image (=the digital echo signal) of those lines is stored in a given pixel which is shifted by one pixel in the X direction from its originally-designated pixel.

After the image data has been temporarily stored in the frame memory 4, it is read out by the readout address of the address generator 7. The address signal is sequentially generated in synchronism with the television scanning time and coincident with the television scanning direction. As seen from the display of the TV monitor 9, since the image data of the frame memory 4 is stored in the given pixels corresponding to the travelling direction of the ultrasonic beam 30, when it is displayed on the TV monitor 9, the sector-shaped image (=tomographic image) of the object 20 can be observed. The reason is that the image data exists only in the pixels in coincident with the travelling directions of the ultrasonic scanning lines 30, i.e., the sector shaped memory region of the frame memory 4 (See FIG. 1).

In the ultrasonic examination apparatus 100, the following linear interpolation may be further performed. That is, 128 ultrasonic scanning lines 30 exist in the sector scanning range. Under these circumstances there are many pixels into which no echo signal is stored in the X direction of the frame memory 4, in accordance with the depth direction with respect to the transducer 1. In other words, the deeper the scanning line travels inside the object 20, the larger the number of the non-used pixels becomes with respect to the adjacent scanning lines. As a result, the image density of the displayed tomographic image becomes coarse.

Accordingly, the interpolation data is calculated based upon the image data of the given scanning line. That is, this image data is utilized for that of the pixel in which no image data is stored and which is located between the adjacent scanning lines 30. Due to this linear interpolation, the image quality can be further improved.

After the readout operation by the address generator 7, the output image signal is converted into the analogue image signal by the D/A converter 8. Then the analogue image signal is processed to produce the standardized television composite signal. Finally this composite signal is displayed on the TV monitor 9 as the tomographic image of the object 20.

In accordance with the present invention, the shapes of the central scanning lines which are displayed on the TV monitor 9 become a zig-zag line because of the wobbling processing. Thus the false contour that is caused by the exceeding pixelizing, or digitizing precesion can be diminished, or avoided. Moreover since the wobbling processing is effected only for the central and its adjacent scanning lines, the entire image quality is not degraded, but the better image can be realized for diagnostic purpose.

Figure 5A:
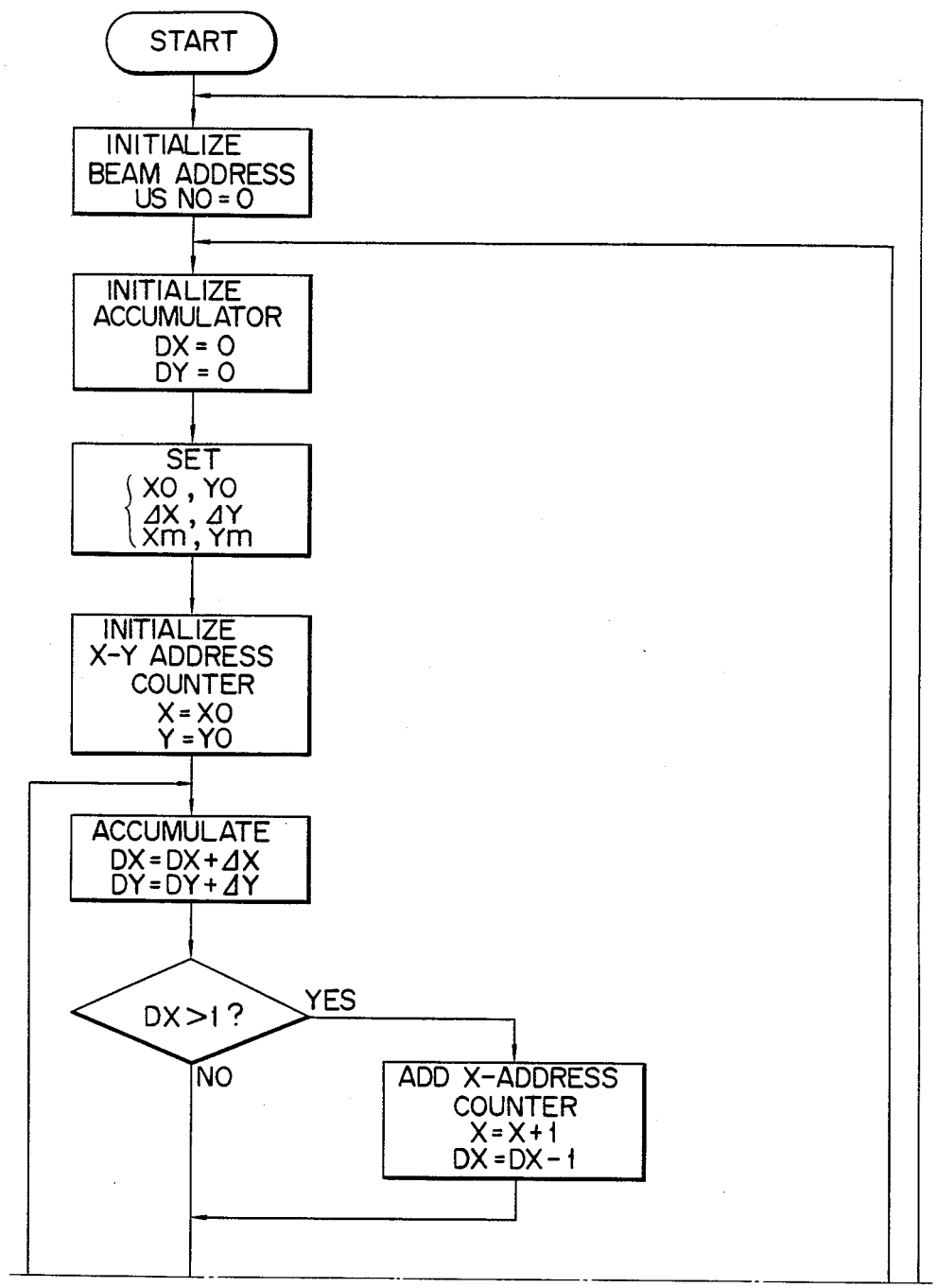
FIGS. 5A and 5B show a flow chart demonstrating the operation of the address generator for write operation shown in FIG. 3.
Figure 5B:
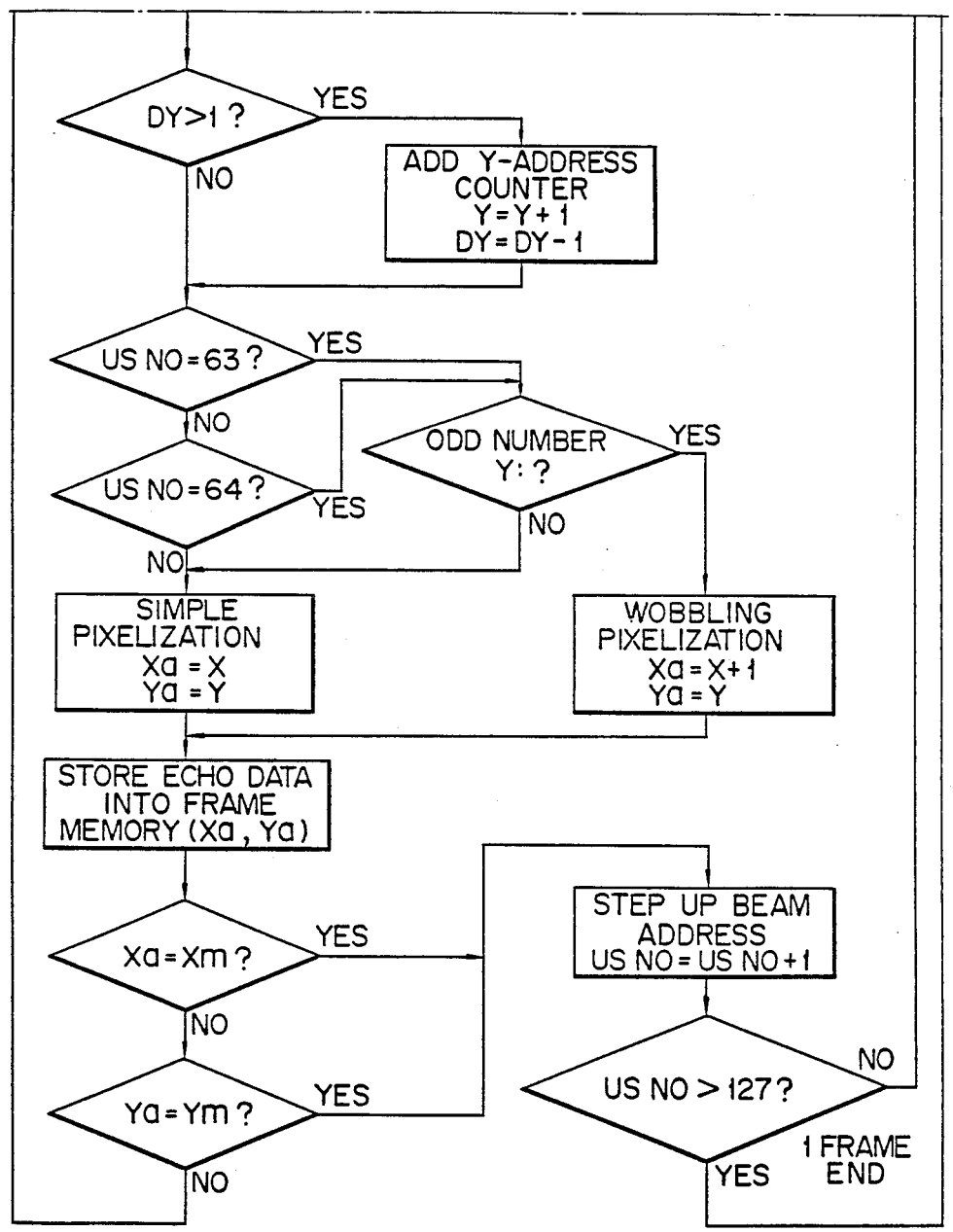

Referring to the flow chart as shwon in FIG. 5, the entire operation of the address generator for write operation 6, especially the detailed operation of the unit vector generator 61, accumulator 62 and wobbling processor 64 will now be summarized. In this flow chart, the indication "US" denotes the ultrasonic beam.

As an initial condition, the address generator for ultrasonic beams 5, the unit vector accumulator 62, and the X-Y address counter 63 are initialized. At the same time, central addresses of the sector scanning lines, the unit vectors (ΔX, ΔY), and peripheral addresses of the sector scanning lines (Xm, Ym) are preset.

Then, the accumulation is carried out in the unit vector accumulator 62, the counter operation is effected in the X-Y address counter 63, and a decision is made whether the counter value Y is an odd number or not. If yes, then the simple pixelizing operation (processing) is carried out. If no, then the wobbling pixelizing operation is carried out in the wobbling processor 64.

It should be noted that as previously described, it is possible to omit the simple pixelizing operation in the above processing, so that the digital scanning data is merely stored in the frame memory 4 without the simple pixelizing operation, and only the wobbling processing is carried out.

While the present invention has been described using a specific embodiment, it should be understood that further modifications and changes can be made without departing from the scope of the present invention. For example, it is possible to examine the material instead of the patient, which is so-called as the non-destructive examination.

Further there are many possibilities to perform the wobbling processing to not only the two central scanning lines, but also the other scanning lines along which the false contour appears remarkably.

In the previous embodiment, the central scanning lines were a zig-zag line. It is of course possible to employ certain pattern for the scanning lines.

What is claimed is:

1. An apparatus for examining an object ultrasonically comprising:
   (a) ultrasonic transducer means for directing ultrasonic beams in a sector toward said object and for receiving echoes of said ultrasonic beams reflected from said object to produce electronic echo signals;
   (b) analog-to-digital converting means, coupled to said ultrasonic transducer means, for converting said echo signals into digital data at a sampling rate;
   (c) memory means, coupled to said analog-to-digital converting means and, for temporarily storing each of said digital data into corresponding ones of a plurality of pixels, said plurality of pixels being arranged in a matrix of lines and columns corresponding to coordinates of said ultrasonic beams in said sector, and said pixels being uniquely identified by a line address and a column address;
   (d) writing means, coupled to said memory means, for dithering said column addresses for said echo signals and for writing said digital data into said pixels of said memory means using said dithered addresses, wherein said address dithering includes changing said column addresses by a preset amount; and
   (e) means, coupled to said memory means, for reading said data from said memory means and for displaying said data.

2. The apparatus according to claim 1 wherein said writing means includes means for dithering said column addresses only for beams within a small angle in the center of said sector.

3. The apparatus according to claim 1 wherein said writing means further includes
   a unit vector generator for generating unit vectors corresponding to the directions of said beams;
   a unit vector accumulator for accumulating the unit vectors derived from said unit vector generator in synchronism with said sampling rate of said analog-to-digital converting means;
   an address counter for counting accumulated unit vectors to produce said column and line addresses; and
   means for dithering said column address by a single pixel.

4. The apparatus according to claim 1 further including scanning means for steering said ultrasonic beam throughout a sector in a plane intersecting said object and for routing said echo signals to said analog-to-digital converting means.

5. The apparatus according to claim 4 further including means for generating addresses for said scanning means and for said writing means to provide synchronization.

* * * * *